(12) United States Patent
Jung

(10) Patent No.: US 7,449,296 B2
(45) Date of Patent: Nov. 11, 2008

(54) METHOD AND KIT FOR DETECTING PORCINE REPRODUCTIVE AND RESPIRATORY SYNDROME VIRUS

(75) Inventor: Dong-Hyuk Jung, Hwaseong (KR)

(73) Assignee: MJ Biologics, Inc., Mankato, MN (US)

( * ) Notice: Subject to any disclaimer, the term of this patent is extended or adjusted under 35 U.S.C. 154(b) by 97 days.

(21) Appl. No.: 11/361,184

(22) Filed: Feb. 24, 2006

(65) Prior Publication Data

US 2007/0004006 A1    Jan. 4, 2007

Related U.S. Application Data

(60) Provisional application No. 60/657,609, filed on Feb. 28, 2005.

(51) Int. Cl.
*C12Q 1/68* (2006.01)
(52) U.S. Cl. .................... 435/6; 435/7.1
(58) Field of Classification Search .............. 435/6, 435/7.1
See application file for complete search history.

(56) References Cited

U.S. PATENT DOCUMENTS

| 4,235,601 | A | 11/1980 | Deutsch |
| 5,591,645 | A | 1/1997 | Rosenstein |
| 2003/0186225 | A1 | 10/2003 | Paul et al. |
| 2006/0127885 | A1 | 6/2006 | Kang et al. |

FOREIGN PATENT DOCUMENTS

| WO | WO/96/06619 A1 | 3/1996 |
| WO | WO/99/39582 A1 | 8/1999 |
| WO | WO00/53787 A1 | 9/2000 |
| WO | WO02/095040 A1 | 11/2002 |

OTHER PUBLICATIONS

Cancel-Triado et al (Veterinary Immunology and Immunopathology, 2004, vol. 102, pp. 249-262.*
Teifke, J.P., et al. "Detection of European Porcine Reproductive and Respiratory Syndrome Virus in Porcine Alveolar Macrophages by Two-colour Immunofluorescence and In-situ Hybridization-immunohistochemisry Double Labelling", *J. Comp. Path* (2001) 124:238-245.
Meulenberg, J.J. M., et al. Localization and Fine Mapping of Antigenic Sites on the Nucleocapsid Protein N of Porcine Reproductive and Respiratory Syndrome Virus with Monoclonal Antibodies, *Virology* (1998) 252:106-114.
Yang, L., et al. "Antigenic and genetic variations of the 15 kD nucleocapsid protein of porcine reproductive and respiratory syndrome virus isolates", *Arch Virol.* (1999) 144:525-546.

* cited by examiner

*Primary Examiner*—Ali R. Salimi
(74) *Attorney, Agent, or Firm*—Patentique PLLC

(57) ABSTRACT

The invention provides methods, devices, and kits for the detection of a class of porcine reproductive and respiratory syndrome (PRRS) virus, or PRRSV, in a biological fluid. The invention is based in part on an agent which binds the nucleocapsid (N) protein of PRRSV. The agent may be an antibody that binds the N protein with specificity. Compositions and devices comprising the binding agent, as well as methods of using it are also provided. Also provided are methods of preparing devices and kits for the practice of the methods.

20 Claims, 2 Drawing Sheets

METHOD AND KIT FOR DETECTING PORCINE REPRODUCTIVE AND RESPIRATORY SYNDROME VIRUS

RELATED APPLICATION

This application claims benefit from Provisional U.S. Patent Application 60/657,609, filed Feb. 28, 2005, which is hereby incorporated by reference as if fully set forth.

FIELD OF THE INVENTION

This invention relates to methods, devices, and kits for the detection of a class of porcine reproductive and respiratory syndrome (PRRS) virus, or PRRSV, in a biological fluid. The invention is based in part on an agent which binds the nucleocapsid (N) protein of PRRSV. In some embodiments, the agent is an antibody that binds the N protein with specificity. Compositions and devices comprising the binding agent, as well as methods of using it are also provided. Also provided are methods of preparing devices and kits for the practice of the methods.

BACKGROUND OF THE INVENTION

A major cause of economic losses in the U.S. swine industry is porcine reproductive and respiratory syndrome (PRRS) virus, or PRRSV. PRRSV is the causative agent of reproductive failure and respiratory disorders in pigs. The economic losses associated with PRRS are mainly due to its involvement in abortion in pregnant females and respiratory disease complex (PRDC) in growing pigs. Different control measures including the use of vaccine and management change have been practiced. See U.S. Pat. No. 5,690,940, for example. Despite routine vaccination, however, it is not uncommon for outbreaks of PRRSV to occur on swine farms.

Thus, eradication of the disease using PRRSV vaccine has not been routinely successful at the farm level. Methods such as total depopulation and repopulation have shown to be effective for on-farm eradication. However, such methods cannot be used in every farm and is relatively expensive to perform.

Moreover, such methods are dependent upon detection of PRRSV. The nucleic acid sequences and encoded proteins of some PRRSV strains have been described. The detection of PRRSV via tissue samples, including lung tissue, has also been discussed (see WO 96/06619), which is consistent with the observation that PRRSV preferentially replicates in alveolar lung macrophages. After infection by the oronasal route, PRRSV replicated in lung macrophages proceed to the lung lymph nodes and then to peripheral lymph nodes, spleen, and bone marrow.

Citation of documents herein is not intended as an admission that any is pertinent prior art. All statements as to the date or representation as to the contents of documents is based on the information available to the applicant and does not constitute any admission as to the correctness of the dates or contents of the documents.

BRIEF SUMMARY OF THE INVENTION

This invention provides an agent that binds the nucleocapsid (N) protein of porcine reproductive and respiratory syndrome (PRRS) virus, or PRRSV. The agent may be used in methods, devices, and kits for the detection of PRRSV in a biological fluid via the detection of the presence of the N protein in the fluid. The invention is based in part on the unexpected discovery that the N protein is detectable in biological fluids of PRRSV infected subjects such that the presence of N protein serves as an indicator of PRRSV infection.

Thus in a first aspect, the invention provides a method of detecting N protein in a sample of a biological fluid from a subject, such as an individual suspected of being infected with PRRSV. The method comprises contacting the sample, or a diluted form thereof, with a binding agent which binds the N protein of PRRSV. The binding of the agent to the N protein forms a complex, which may be detected to indicate the presence of the N protein, and thus optionally the presence of a PRRSV infection in the subject from which the sample was obtained. The sample is preferably from a porcine subject, but any subject which may be infected by PRRSV or a PRRSV carrier may be used in relation to the present invention.

The biological fluid may be any fluid in which N protein and/or PRRSV particles may be detectably present. Non-limiting examples include the bodily secretions of a subject, such as saliva, tears, mucous, nasal discharge, and vaginal secretions as well as other bodily fluids such as blood, serum, plasma, semen, seminal fluid, and urine as well as any fluid component of feces or a fluid extract of feces.

The binding agent which binds the N protein of PRRSV may be an antibody, or derivative thereof, although non-antibody agents may also be used. The antibody may be prepared by use of a recombinantly produced N protein antigen expressed from ORF7 (open reading frame 7) of PRRSV. Preferably, the antibody is a monoclonal antibody. Such binding agents are an additional aspect of the invention in that they may be applied in the methods described herein as well as in compositions, devices and kits as provided below. In particular, binding agents may also be used to immobilize the N protein, or a macromolecular complex containing it, to facilitate its detection.

Thus the present invention also provides for labeled forms of the binding agent to facilitate its detection when bound to N protein. The binding agent may be labeled to permit direct detection, such as by conjugation to a particulate label which is visible to the eye upon sufficient aggregation. Alternatively, the binding agent may be labeled for indirect detection, such as by conjugation to an enzyme which is detected based upon its activity on a detectable substrate or to produce a detectable product. Of course the binding agent may also be unlabeled and then detected based upon use of a detectable reagent which binds the binding agent. As a non-limiting example with the use of an antibody as the binding agent, the complex of the antibody bound to the N protein may be detected by a detectably labeled secondary antibody which binds the antibody bound to the N protein.

In another means to facilitate the detection of the binding agent when bound to N protein, the invention provides for the immobilization of a complex comprising the binding agent bound to the N protein. In some embodiments, the immobilization is to a solid substrate comprising an immobilized second binding agent which binds and immobilizes the complex. A non-limiting example of such an embodiment includes a situation where the second binding agent localizes the complexes in a small area to improve the ease of detecting them. In another non-limiting embodiment, the immobilization forms a "sandwich" wherein the N protein is "sandwiched" between the binding agent and a second agent immobilized on a solid substrate which also binds N protein.

In a further aspect of the invention, devices for the practice of the above described methods are provided. Generally, such devices are for detecting the presence of N protein in a sample of a biological fluid as an indicator of PRRSV infection in the subject from which the sample was taken. Thus the devices may be used as a rapid means of diagnosing the presence of PRRSV infection.

In some embodiments of the invention, such a device comprises a test strip which is optionally uniform in composition. Alternatively, the test strip is non-unitary in construction but the different components are functionally linked as provided below. In addition to embodiments wherein the device is simply a test strip, the invention also provides for devices wherein the test strip is embodied within a housing or casing of liquid impermeable material to facilitate the manipulation and use of the test strip.

At the heart of such a device of the invention is the presence of both a first binding agent which binds N protein of PRRSV to form a complex and a second binding agent which immobilizes the complex. The first binding agent may thus be viewed as a "detector agent" and is as described herein. Where the first binding agent is an antibody, it may be viewed as a "detector antibody". The first binding agent is located in a mobilizable form on a first portion of the device. A non-limiting example of such a mobilizable first binding agent includes the drying of the agent on a first portion of a device such that upon hydration with a liquid, such as a sample of a biological fluid, the agent is mobilized within the sample and thus may move with the liquid. Where the liquid, such as a sample of a biological fluid, contains N protein, the first binding agent binds the N protein to form a complex which moves with the liquid.

The second binding agent is immobilized on a second portion of a device such that it will bind and immobilize a complex of the first binding agent and N protein when such a complex is brought into contact with the second binding agent. The second binding agent may thus be viewed as the "capture agent", or in the case of an antibody as the second binding agent, a "capture antibody". Contact between the second binding agent and the complex occurs via the movement of a liquid containing the complex, such as a sample of a biological fluid that contains a complex of N protein and mobilized first binding agent as described above, into contact with the second binding agent. Such movement is readily accomplished by the first and second portions of the device being in fluid communication with each other such that fluid in the first portion will move into and through the second portion. Such fluid communication may be direct, with no intervening material between the first and second portions, or indirect, with an intervening material between the first and second portions that permits liquid to pass from the first to second portions.

Detection of immobilized complex in the device, preferably by detection of a detectably labeled first binding agent immobilized in the second portion as permitted by the device, may be used to indicate the presence of N protein in a sample of biological fluid. The presence of N protein may be used as an indication of PRRSV infection in the subject from which the sample was obtained. The sample is preferably from a porcine subject, or other subject suspected of being infected with PRRSV, but any subject which may be infected by PRRSV or a PRRSV carrier may be used in the devices of the invention.

The range of biological fluids which may be used in a device of the invention includes any fluid in which N protein and/or PRRSV particles may be detectably present. Non-limiting examples have been provided above and below, and dilutions of such fluids may of course also be used as the sample with a device of the invention.

The range of the first binding agent in a device of the invention includes any that binds the N protein of PRRSV.

The agent may be an antibody, or derivative thereof, as well as a non-antibody agent as described above and below. Preferably, the agent may be located by drying into a mobilizable form as described herein. As may be needed in some embodiments of the invention, mobilization of a first binding agent may be facilitated by one or more mobilization agents that are present in the first portion of the device to improve the mobilization of the first binding agent upon hydration. In some embodiments of the invention, the first binding agent is a monoclonal antibody.

The first binding agent is also optionally labeled as described above and below. Preferably, the nature of the label permits direct detection of the first binding agent, or a complex comprising it. Non-limiting examples of such labels for direct detection include a particulate label.

The second binding agent of a device of the invention binds and immobilizes a complex comprising the first binding agent bound to the N protein. The immobilization is preferably to an area within the second portion of the device that facilitates detection of the complexes. In some embodiments, the second binding agent is an antibody, preferably one which binds the N protein or an epitope present on a complex of the N protein and the first binding agent. Thus the device would permit the formation of a "sandwich" wherein the N protein is "sandwiched" between the first and second binding agents and immobilized on the second portion of the device. In additional embodiments of the device, the second binding agent is the same as the first binding agent.

As described above, the first and second portions of such a device of the invention may be made of the same or different materials. In either case, the material used for the two portions must permit fluid communication between them. The nature of such materials is thus broad and may be a wide range of solid materials that permit the passage of fluids by capillary action (capillarity), wicking, imbibing, or other equivalent actions. Such materials may be porous or bibulous as well as non-bibulous or membranous in nature. In some embodiments wherein the first and second portions are composed of different materials, the first portion may be a porous pad of material while the second portion may be a membrane in fluid communication with the first portion. Of course such a construct may be within a housing or casing as described herein.

Such a housing or casing may include an aperture or opening to permit contact of the device with a sample of a biological fluid. The contact may be to the first portion, and the aperture or opening may be optionally removably covered to prevent contamination or accidental application of liquids to the device. The housing or casing may also include an aperture or opening for observation and detection, within the second portion of the device, of the presence of a complex of N protein and the first binding agent. This aperture or opening may also be optionally removably covered or fitted with a transparent material to provide a window into the device. Of course a housing or casing may also be of a non-encapsulating nature such that the first and second portions are generally available for use without the need for specific apertures or small openings in the housing or casing.

A device of the invention may include additional components beyond the first and second portions with an optional housing or casing. One optional component is a sample application pad in fluid communication with said first portion. Such a pad may also be of a porous, bibulous, or membranous material that permits the passage of fluids by capillary action (capillarity), wicking, imbibing, or other equivalent actions to the first portion. Where such a pad is present, a sample for use with the device is applied to the pad. Accordingly, any aperture or opening, as described above, for the contacting of, or application of, a sample with the device would be located to permit access to the application pad.

Another optional component is an absorbent pad in fluid communication with said second portion. Such a pad may again be of a porous, bibulous, or membranous material that permits the passage of fluids from the second portion by capillary action (capillarity), wicking, imbibing, or other equivalent actions. Such a pad acts as a reservoir or "sink" for liquid in the second portion such that excess liquid in the second portion will move away therefrom to permit additional fluid to travel from the first portion to the second portion. Such an absorbent pad need not be directly accessible via an aperture or opening of the device, but preferably is of a size which permits retention of a volume of liquid larger, or slightly larger, than the volume of a sample used with the device.

A further optional component is a control site or control region within the device of the invention which confirms the proper functioning of the device regardless of whether N protein was present in a sample applied to the device. Such a site or region is preferably located downstream of the flow path defined via movement of liquid from the first portion to the second portion and preferably includes a reagent that indicates a sample has passed through the first and second portions of the device. Such a site or region would thus be in between the second portion and an optionally present absorbent pad but still permit fluid communication between the second portion and the absorbent pad. The reagent may be one which produces a color upon being wetted or one which binds, and thus permits the detection of, a labeled first binding agent regardless of whether it has bound N protein. Such a site or region may be visible via the same aperture or opening, if present, for observing the second portion or via an additional aperture or opening in a device of the invention.

While the various aspects of the invention are contemplated for use in relation to a variety of PRRSV strains other than the Lelystad isolate prevalent in Europe, the agents, methods, and devices of the invention preferably relate to the binding, and thus the detection of, the N protein of North American and Korean serotypes of PRRSV. Moreover, the invention may be used in relation to other strains of PRRSV related to North American and Korean strains, including other Asian serotypes as well as North American or U.S. like strains of PRRSV found in Europe, Asia, and South America. Therefore, the invention may be more generally viewed as a method of detecting the N protein of any PRRSV that reacts with the N protein binding agents of the invention.

Additionally, methods relating to the production of such devices are provided. One additional aspect of the invention is a method of preparing components of the devices described herein. One method is the immobilization of a first binding agent, particularly an antibody that binds the N protein of PRRSV, in a mobilizable form on a first portion of a device as described herein. Preferably, the method is the drying of the first binding agent to a test strip, or portion thereof, of the invention. The first binding agent is preferably labeled as described herein prior to immobilization.

Another method is the immobilization of a second binding agent, which may also be an antibody that binds the N protein of PRRSV, in a non-mobilizable form to a second portion of a device as described herein. Preferably, the method is the conjugation, or other irreversible linkage, of the second binding agent to a test strip, or portion thereof, of the invention. The immobilized second binding reagent is used to bind and immobilize a complex of N protein and the first binding agent, and may be the same as the first binding agent in an unlabeled form in some embodiments of the invention. Of course the methods of locating at least one first binding agent and immobilizing at least one second binding agent may be performed together on a device or test strip, or portion thereof, of the invention.

In further aspects of the invention, compositions and kits comprising the binding agents of the invention are provided. Non-limiting examples of such compositions include those containing a binding agent which binds N protein of PRRSV in the presence of one or more reagents to label the binding agent or to facilitate its immobilization, in a mobilizable form, on a device of the invention. Another non-limiting example of such compositions is one containing a second binding agent as described above with one or more reagents to facilitate its immobilization on a device or solid substrate of the invention. Non-limiting examples of kits include those comprising one or more agents of the invention, or one or more devices of the invention, for use in the methods disclosed herein.

The details of one or more embodiments of the invention are set forth in the accompanying drawings and the description below. Other features, objects, and advantages of the invention will be apparent from the drawings and detailed description, and from the claims.

DEFINITIONS

Figure 1:
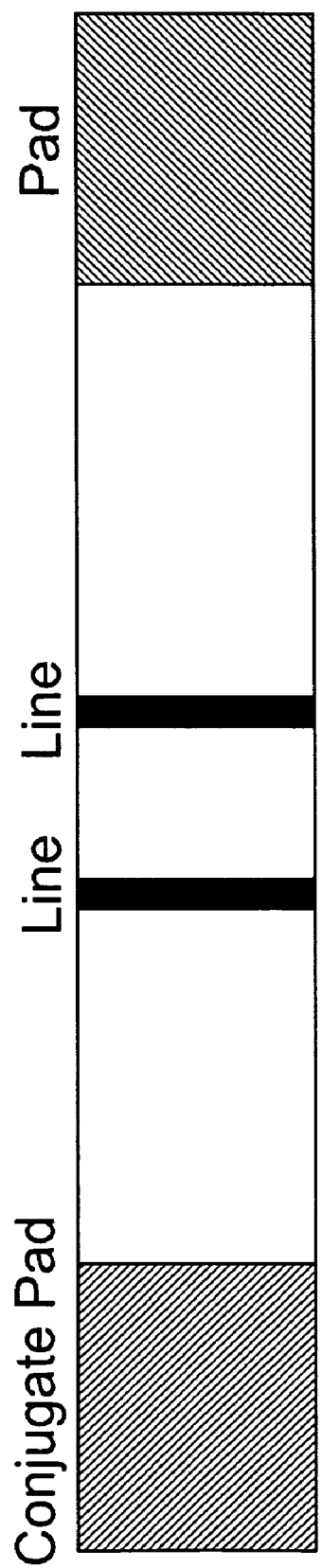
FIG. 1 provides an illustration of one device of the invention. The view is from the top of a device without a separate Sample Pad for the application of a sample to the device. The device may thus be modified to include a Sample Pad or be used with direct application of the sample to the Conjugate Pad.

As used herein, the terms porcine reproductive and respiratory syndrome (PRRS) virus, or PRRSV, refer to a virus which causes PRRS, Mystery Swine Disease (MSD), Swine Infertility and Respiratory Syndrome (SIRS) which was previously known as "blue-eared syndrome", porcine epidemic abortion and respiratory syndrome (PEARS), Wabash syndrome, mystery pig disease (MPD), swine plague, blue abortion disease or blue ear disease in the United Kingdom, abortus blau in the Netherlands, seuchenhafter spatabort der schweine in Germany, and Heko-Heko disease.

The terms "nucleocapsid protein" or "N protein" of PRRSV as used herein refer to the polypeptide encoded by ORF7 of a PRRSV genome as understood in the art. The polypeptide has been reported to be highly conserved among North American PRRSV isolates and is known to include at least two antigenic domains designated B and D (see for example WO 00/53787, pages 9-10). The amino acid sequence QLCQLL (SEQ ID NO:1) is part of the B domain while the sequences of PEKPHFPLAAEDDIRHH (SEQ ID NO:2) and ISTAFNQGAGT (SEQ ID NO:3) are part of the D domain. But the invention is not limited to the detection of N proteins containing these sequences from WO 00/53787. Without being bound by theory, and offered to improve the understanding of the invention, these sequences, from WO 00/53787, are not believed to be required for recognition of N protein because this invention is based in part on the ability to recognize N proteins with the sequence QLCQML (SEQ ID NO:4) in the B domain and the sequences PEKPHFPLAT-EDDVRHH (SEQ ID NO:5) and TQTAFNQGAGT (SEQ ID NO:6) in the D domain. These sequences are similar, but not identical, to the sequences provided above from WO 00/53787. The invention is also not limited to the detection of N proteins containing the latter three sequences.

DETAILED DESCRIPTION OF MODES OF PRACTICING THE INVENTION

The invention provides a binding agent capable of binding N protein from PRRSV in a sample of a biological fluid from an animal subject. Preferably, the binding agent specifically binds the N protein to the exclusion of other molecules present in the biological fluid. In many embodiments of the invention, the subject is a pig, and thus the sample may be of a bodily fluid or secretion from a pig. Non-limiting examples of pigs that from which samples may be obtained for use with the present invention include boar, sow, fattener, and gilt. The pigs may range in age from 1 to about 30, 30 to about 40, 41 to about 50, or 51 to about 60 days or older.

The binding agent is preferably able to bind a N protein as found in multiple PRRSV strains and isolates. In other embodiments of the invention, the binding agent may optionally not cross react with other porcine viruses, such as circovirus, porcine parvovirus (PPV), Japanese encephalitis virus (JEV), rotavirus, pseudorabies, encephalomyocarditis virus, swine influenza virus, and transmissible gastroenteritis (TGE) virus. Examples of PRRSV include, but are not limited to, VR2332, VR2385/VR2386 (ISU-12), VR2429 (ISU-22), VR2430 (ISU-55), VR2431 (ISU-3927), ISU-79, ISU-1894, PL96-1, PL96-7, PL97-1/LP1, and CNV-1.

The binding agent is preferably a PRRSV-specific antibody, or a fragment thereof, which binds the N protein of PRRSV. Accordingly, the invention may be considered as providing immunochromatographic based methods for the detection of PRRSV. The antibodies of the invention may be polyclonal but is preferably monoclonal. The antibodies may also be fragments such as the Fv or Fab regions of an N protein binding antibody. Other non-limiting embodiments include single chain antibodies, including single chain Fv regions and single chain Fab regions.

The N protein binding antibodies may be generated by any appropriate method known in the art. In some embodiments of the invention, the antibodies are generated by use of a recombinantly produced N protein. Such a protein may be expressed in a eukaryotic cell or a bacterial cell such as *E. coli*.

In preferred embodiments of the invention, the antibodies of the invention are from a species which has been extensively used to generate primary antibodies for use in diagnostic assays. Non-limiting examples include mouse and rat antibodies. The antibodies are preferably of the $IgG_1$ isotype, although the use of other antibody isotypes is contemplated for the practice of the invention. The use of well characterized species to produce antibodies of the invention also facilitates their use with a secondary antibody as described herein. Non-limiting examples of such secondary antibodies include those from specific animals, e.g., goat, rabbit, etc., which recognize the Fc portions of the antibody used as the binding agent.

Specific examples of N protein binding antibodies that may be used in the practice of the invention include MAb 122.17, which recognizes the D domain of N protein (see WO 02/095040); PP7eF11 (see WO 99/39582); and SDOW-17 (see WO 96/06619). In a particularly preferred embodiment of the invention, the antibody is the MAb identified as BIT 12D9 produced by a murine cell line and deposited as Deposition No. KCTC 10775 BP at the Korean Collection for Type Cultures on Feb. 1, 2005.

As explained herein, the binding agent of the invention may be labeled to facilitate its detection. Thus the invention provides for the modification of the binding agent by attachment of another moiety thereto. The moiety is preferably a detectable label, including a directly detectable label such as a radioactive isotope, a fluorescent label (Cy3 and Cy5 as non-limiting examples) or a particulate label. Non-limiting examples of particulate labels include latex particles, metal sols, and colloidal gold particles. Alternatively, the label may be for indirect detection. Non-limiting examples include an enzyme, such as, but not limited to, luciferase, alkaline phosphatase, and horse radish peroxidase. Other non-limiting examples include a molecule bound by another molecule, such as, but not limited to, biotin, an affinity peptide, or a purification tag. Preferably, the label is covalently attached.

The binding agent of the invention may be used in methods of detecting N protein in a sample of a biological fluid from a subject as described herein. While the sample may be used directly, it may also be diluted prior to use. Non-limiting examples include a diluent containing EDTA or other divalent cation chelator used in a 1:1 ratio with a sample of biological fluid from a subject. Other embodiments of the invention include use of a diluent of from 1-5% bovine serum albumin in 0.01M $KH_2PO_4$ and $Na_2HPO_4$ and 0.1% sodium azide with a semen sample as non-limiting examples. In other embodiments with serum or plasma samples, dilution may be omitted. The sample is preferably from an individual suspected of being infected with PRRSV due to the presence of symptoms indicative of an infection. Alternatively, the methods of the invention may be used as part of routine screening of animals, such as those of a farm to permit rapid identification and isolation of infected individuals. The methods may also be used in specific instances, such as prior to transport or transfer of an animal from one location to another to permit identification of infection and prevent spread of infection.

The methods of the invention are based upon the formation of a complex comprising the N protein of PRRSV bound to a binding agent as described herein. Optionally, more than one binding agent is used to form at least one complex. The at least one binding agent is preferably labeled to improve the ease of detecting the complex. Formation of at least one complex after contact of a sample with at least one binding agent indicates the presence of PRRSV in the subject from which the sample was obtained.

The at least one complex may also be immobilized to facilitate its detection. As a non-limiting example, the complex may be immobilized by binding to a second binding agent immobilized to a solid substrate, such as a surface of a well, plate, dish or tube. The complex may then by detected based on localization on the surface. Alternatively the solid substrate may be a bead or chromatographic media which permits detection based on localization on the bead or media. The second binding agent preferably binds the N protein or an epitope present in the complex of N protein and the binding agent as described above. Alternatively, the second binding agent is the same as the binding agent.

Without being bound by theory, and offered solely in the interest of improving the understanding of the invention, the use of the same binding agent to both bind N protein to form a complex and immobilize said complex may occur based on the presence of two or more binding sites on N protein for binding by the binding agent. Alternatively, the binding agent may be binding to a macromolecule complex, such as, but not limited to, a PRRSV particle, comprising more than on N protein.

The binding agents of the invention may also be used in devices for the practice of the methods of the invention. As noted above, use of an antibody or N protein binding fragment or derivative thereof, in such devices may be considered as rendering them immunochromatographs.

In one simple form, a device of the invention is a test strip. The test strip may be designed to operate solely based on the liquid available from a sample applied thereto (see for example U.S. Pat. No. 5,591,645 for analogous test strip embodiments). Alternatively, the test strip may be designed to operate in connection with a solvent or developing solution which increases the volume of the sample applied to the test strip (see for example U.S. Pat. No. 4,235,601 for analogous embodiments). In some embodiments of the invention, however, the test strip is embodied in a housing or casing, preferably composed of a plastic, polyacrylate or other liquid resistant material, to form a device of the invention. The test strip may include a backing composed of similar materials.

The test strip may be uniform in composition, such as by being a unitary membrane strip comprising the first and second portions as described herein. Non-limiting examples include a strip of nitrocellulose membrane of appropriate pore size. Non-limiting examples of pore sizes include those in the range of 1-250 microns. Other non-bibulous materials may also be used, along with one or more mobilization agent as described herein to improve the mobilization of a dried first binding agent (the detector agent or preferably the detector antibody). Non-limiting examples of a mobilization reagent include glazes comprising sugar and/or BSA (bovine serum albumin).

Alternatively, the test strip is non-unitary in construction but the different components are functionally linked to permit fluid communication therebetween. In some embodiments, the first portion of the test strip as defined herein is composed of a porous or bibulous material. Non-limiting examples include cellulose or glass wool.

Placement of the first binding agent in a mobilizable form on the first portion of a device of the invention is preferably by drying a solution containing the agent thereon. In some embodiments, the solution is sprayed on and then dried prior to use. A non-limiting representative example of such a solution is one containing a detector reagent of the invention. Preferably, the first binding agent is labeled as described herein, such as with colloidal gold as a non-limiting example.

Non-limiting methods for 1) the preparation of a colloidal gold solution; 2) conjugation of antibody to the colloidal gold; and 3) treatment of the conjugate pad are provided in the Example section below. Non-limiting methods for the immobilization of a capture antibody are also provided.

A test strip or other device of the invention may also comprise a control site or control region as described herein. The control site or region may comprise a reagent that produces a color upon being wetted. Non-limiting examples include cobalt chloride, copper chloride, and the like. Alternatively, the reagent may be a pH indicator which exhibits a color at the pH of the traversing fluid different from the color in the dry state. In a further alternative, the reagent is one which binds, and thus permits the detection of, a labeled first binding agent regardless of whether it has bound N protein. A non-limiting example in the case of an antibody as the first binding agent is a secondary antibody as described herein and immobilized at the control site or region. As a non-limiting example, an anti-mouse IgG antibody may be used at the control site or region to bind and immobilize a mouse IgG antibody that binds N protein, such as a MAb that binds N protein specifically.

The binding agents, compositions, methods, and devices of the invention are suitable for the preparation of kits produced in accordance with well known procedures. The invention thus provides kits comprising the binding agents as described herein, or compositions or devices comprising them, for use in one or more methods as disclosed herein. Such kits optionally further comprise an identifying description or label or instructions relating to their use in the methods of the present invention. Such a kit may comprise containers, each with one or more of the various reagents (typically in concentrated form) or devices utilized in the methods. A set of instructions will also typically be included.

Kits comprising a device of the invention may further comprise one or more additional reagents or pieces of equipment for use with the device in a method of the invention. Non-limiting examples of additional materials for inclusion are sample diluent solution, diluent vial, and a dropper for transfer of sample.

Having now generally described the invention, the same will be more readily understood through reference to the following examples which are provided by way of illustration, and are not intended to be limiting of the present invention, unless specified.

EXAMPLES

Example 1

Status of PRRSV Infection in South Korea

To investigate the prevalence of PRRSV infection in Korea, porcine sera from fattener, sow, gilt, and boar were collected throughout the country from July 2000 to December 2002 and examined for the presence of PRRSV-specific antibodies by the indirect fluorescence antibody (IFA) test. From a total of 6,696 porcine sera tested, 3,449 were PRRSV positive and so PRRSV infection rate was 51.5%. The PRRSV positive ratios of 1-30, 31-40, 41-50, 51-60 and more than 60 day old fattener pigs were 24.1%, 19.2%, 28.0%, 50.9% and 72.1%, respectively, whereas the ratios of gilt, sow and boar were 55.2%, 21.7% and 33.3%, respectively.

Results showed that the PRRSV positive ratio of pigs increased according to increases in age and was more than 50% for pigs of 51 days or older. Detected antibody from young pigs under 30 days old seemed to be derived mainly from maternal antibody. The low PRRSV positive ratio of pigs between 31 and 40 days old might be due to the decrease of maternal antibody in this period. The increase in PRRSV positive pigs of 41 days or older reflects the start of infection by PRRSV in pigs of about this age.

Example 2

Production of MAb Against the N Protein

ORF7 from a Korean PRRSV isolate (CNV-1 strain) was cloned into an expression vector (PGEM T easy vector system II from Promega) for recombinant production. The expression vector was prepared by ligation of the ORF 7 cDNA and pGEX 4T-1 vector after treatment with BamHI and EcoRI. The cDNA was expressed after transfection into *E. coli*. The expressed N protein was isolated and injected into the food pad of BALB/c mice. Cells expressing antibodies against the expressed N protein were isolated and used to prepare hybridoma cells. Cells were injected intraperitoneally into naïve BALB/c mice to express MAb in abdominal fluids (ascites fluid). Column chromatography packed with resin conjugated with protein A (from Sigma Chemicals or other commercial sources) was used in the process of MAb purification from the fluid.

The resultant MAbs were isotype $G_1$. From a total 15 MAbs produced, all were confirmed as PRRSV N protein specific and the antibody titer of these MAbs ranged from 6,400 to 25,600 by IFA. The reactivity of produced MAbs with different kinds of PRRSV strains and other important porcine viruses, such as porcine circovirus type 2 (PCV-2) and PPV, was examined by IFA.

The MAbs were positive for the PRRSV strains VR2332, PL96-1, PL 96-7, PL 97-1/LP1, and CNV-1 of PRRSV. Twenty-one other isolates were also tested and found to give rise to positive reactions with the MAbs. The MAbs were negative for circovirus, porcine parvovirus, JEV, rotavirus, and TGE in addition to the Lelystad isolate of PRRSV.

Example 3

Further Testing of MAb

One MAb, BIT 12D9 (deposited as described herein) was used to prepare a rapid diagnostic device to test the specificity for PRRSV N protein. The MAb was used as both detector (first binding agent as described in the devices above) antibody and capture (second binding agent as described in the devices above) antibody. The device confirmed that the developed rapid diagnostic kit was PRRSV-specific, because it was reactive with all PRRSVs except for Lelystad strain and negative with other porcine viruses.

The sensitivity of the rapid diagnostic device was also tested using recombinant N protein (rGST-ORF7) expressed in *E. coli* and PRRSV infected tissue culture fluid having a viral titer of 10,000,000 $TCID_{50}$/ml (TCID refers to tissue culture infection dose). The results confirmed that the rapid diagnostic device could detect, as non-limiting examples, 8 ng of rGST-ORF7 and 100 TCID/0.1 ml of PRRSV. Positive reactions were also seen with excess antigen.

Example 4

Preparation of Device

The rapid PRRSV detection device of Example 3 was prepared for use in a method based on membrane-based immunochromatography. The device may be generally described as that of a lateral flow format.

Figure 2:
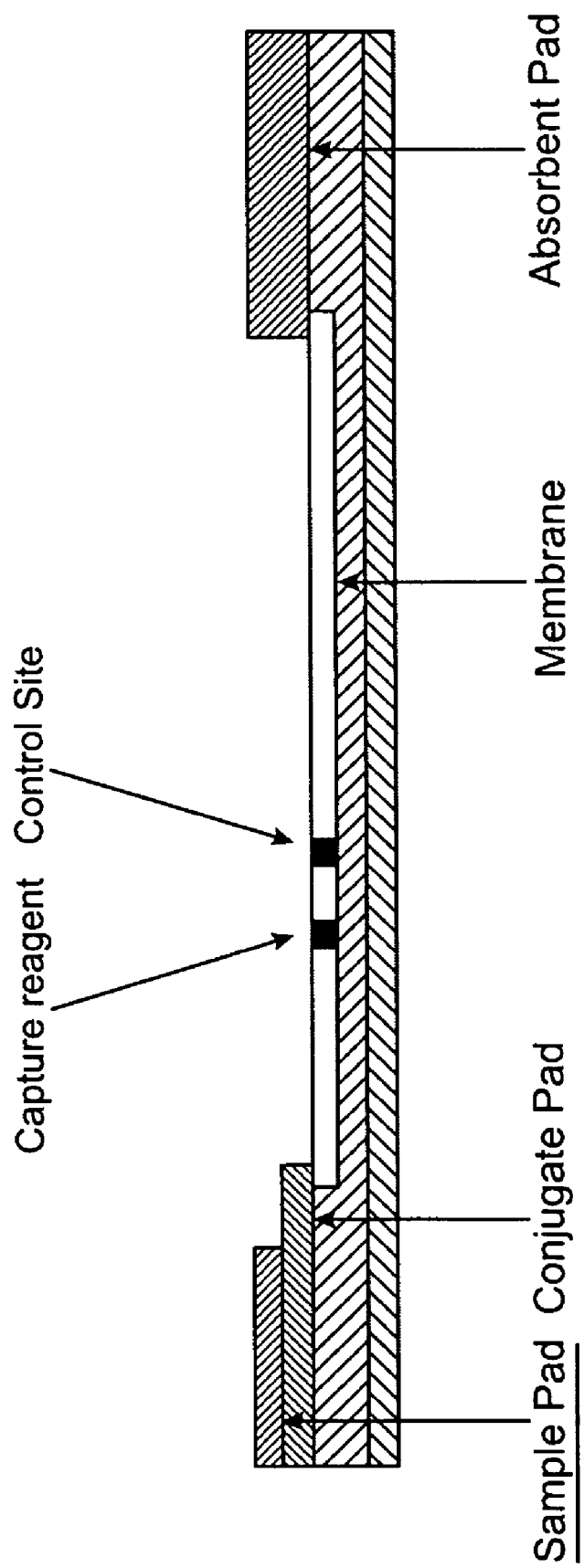
FIG. 2 provides an illustration of another device of the invention similar to that in FIG. 1. The view is from the side of the device with a separate Sample Pad which can convey fluid to the Conjugate Pad, which in turn can convey fluid to the indicated membrane. The membrane can also convey fluid to the Absorbent Pad. The locations of the capture reagent and control site of a device as described herein are shown.

The components of the PRRSV detection device are a sample application pad, conjugate pad, membrane pad and absorbent pad. The device has the general configuration as shown in FIG. 2. The selected PRRSV specific monoclonal antibody (derived from mouse ascites fluid) described above was coupled with colloidal gold and was attached on the conjugate pad. The same monoclonal antibody used as the capture reagent was immobilized on the membrane pad.

Generally, the production of the device may be summarized as follows: 1) preparation of colloidal gold solution, 2) conjugation of antibody to colloidal gold, 3) conjugate pad treatment, 4) sample pad treatment, 5) spraying anti-PRRSV monoclonal antibody and control antibody on nitrocellulose membrane, 6) lamination of the pads and membrane cutting, assembling and packaging, and 7) testing for quality control. These are described in greater detail as follows.

1) Preparation of colloidal gold solution: 1% $HAuCl_4$ solution was added to boiling distilled water at a concentration of 3%, and then 4% citric acid was added to the solution at a concentration of 0.3%. The mixture was cooled at room temperature.

2) Conjugation of antibody to colloidal gold: 100 ml of the colloidal gold solution was prepared to have an optical density value of 10 at 520 nm and adjusted it to be pH 8.5 using $K_2CO_3$. Concentrations of the anti-PRRSV monoclonal antibody and mouse IgG were adjusted to 1.0 mg/ml using 50 mM Tris solution. The antibody (0.5 ml at a time) was added to the colloidal gold solution with stirring, and 10% bovine serum albumin (50 ml) was added after 10 minutes, and then 50 ml of 2% polyethylene glycol in 2 mM sodium tetraborate solution, pH 7.2 was added. The mixture was centrifuged at 20,000 g for 1 hour. The pellet was suspended in 2 mM sodium tetraborate solution at a concentration of 10 by optical density.

3) Conjugate pad treatment: The pad was soaked in 2 mM sodium tetraborate solution and dried in a 30° C. incubator. The dried pad was soaked again in the antibody-gold conjugation solution that was supplemented with sucrose at a final concentration of 5%. Then the pad was dried under conditions of less than 20% humidity.

4) Sample pad treatment: The pad is soaked in 0.01 M $KH_2PO_4$ and $Na_2HPO_4$ (PBS) pH 8.0, and dried in an incubator.

5) Nitrocellulose membrane: Each of the unlabeled anti-PRRSV monoclonal antibody and anti-mouse IgG was adjusted with 0.01M phosphate buffered solution, pH 7.0, to be at 1 mg/ml. Each antibody was sprayed on the membrane 1 μl/cm using a micro-dispenser, and dried in a 30° C. incubator under conditions of less than 20% humidity.

6) Lamination of the pads and membrane cutting, assembling and packaging: The sample pad, conjugate pad, cellulose membrane were attached to a length of an adhesive card, which is immediately below the membrane as shown in FIG. 2. The absorption pad was also attached to the adhesive card at an end distal from the sample pad and conjugate pad (to define a flow path from the sample pad to the absorbent pad) and in a manner permitting fluid flow from the membrane to the absorbent pad (see FIGS. 1 and 2). The laminated card was then cut along the length of the flow path, and each card was placed into a plastic housing or casing with an aperture for sample application to the sample pad and one or more apertures for visual observation of the membrane where the unlabeled monoclonal and anti-mouse IgG antibodies were immobilized (the "Lines" in FIGS. 1 and 2). The final test card may be used immediately or optionally individually wrapped with a dropper and sealed in aluminum foil and stored at room temperature.

7) Testing for quality control: Devices prepared as described above are tested using reference samples. The reference samples include negative, weak positive, medium positive and strong PRRSV positive samples.

With respect to FIG. 1, the Conjugate Pad may be considered a first portion of a device of the invention wherein a first binding agent which binds N protein of PRRSV to form a complex is located in a mobilizable form. In some embodiments, the "Line" closer to the Conjugate Pad is where the second binding reagent of the invention is applied so that it can immobilize N protein in the sample or a complex of N protein and a first binding agent of the invention. This "Line" may thus be viewed as the location of a "capture agent" or "capture antibody" of the invention and thus as the second portion of the device as described herein. The "Line" closer to the Pad (or Absorbent Pad as shown in FIG. 2) may be considered the "control site" or "control region" of the invention and the location of a reagent that indicates sample has passed through the first and second portions of the device.

Although the device does not contain animal serum (containing N protein) as a control, certain test controls have been incorporated to provide information regarding device performance. Specifically, a positive control has been included such that a visible line in a control region forms in the device if the device function properly after addition of sample. No line appears after application of sample if the device failed.

The capture antibody is also immobilized in the shape of a line (in the second portion of the device as described above) such that a visible line appears in the presence of N protein in the sample applied to the device and no line appears in the absence of N protein in the applied sample.

Thus in operation, the device may produce three possible outcomes: no line in the control region, which may indicate device failure (regardless of visible line corresponding to the capture antibody); one line in the control region, which may indicate no N protein and so no virus in the subject from which the sample was obtained; two lines (one in the control region and one corresponding to the capture antibody), which may indicate presence of N protein and so PRRSV positive status. The device is thus simple to use and is analogous to some over-the-counter devices for in home use.

Generally, the device shows positive results with PRRSV containing samples and shows negative results with samples lacking PRRSV.

The device may be provided to a user with the following optional additional materials: a diluent vial, a dropper and a colorless slender plastic tube for sample dilution. Such a combination may be considered a test or diagnostic kit of the invention.

Example 5

Sample Instructions for Use of Device with Blood Serum or Plasma

1) Open the foil package and remove the diluent vial, the dropper, and device.

2) Mix test serum or plasma with diluent in approximately equal volume using the dropper.

3) Place two to four drops of the mixture in the sample aperture of the device which allows contact with the application pad.

4) Let device stand for approximately ten minutes, then read the results. Longer times may result in a false positive.

5) The purple color band only in the "C" area (control region) indicates a negative result. Bands in both the "T" (test or capture antibody region) and "C" areas indicates positive result for PRRSV.

6) A retest should be performed if there is no color on either the "T" test area or the control "C" area.

Note: The presence of EDTA can generate false positive reactions even though the concentration is lower than 0.2%. Check EDTA levels in blood collection tube or other device before use.

Example 6

Sample Instructions for Use of Device with Boar Semen

1) Open the foil package and remove the diluent vial, the dropper, and device.

2) Mix test seminal fluid with diluent approximately in equal volume using the dropper. (A sample collected using a swab can be used by placing the swab into the diluent vial and shaking to release sample.)

3) Collect clear supernatant using the dropper after settlement for a few minutes.

4) Place two to four drops of the solution into the sample aperture of the device which allows contact with the application pad.

5) Let device stand for approximately ten minutes, then read the results. Longer time may cause a false positive.

6) The purple color band only in the "C" area (control region) indicates a negative result. Bands in both the "T" (test or capture antibody region) and "C" areas indicates positive result for PRRSV.

7) A retest should be performed if there is no color on either the "T" test area or the control "C" area.

Note: The presence of EDTA can generate false positive reactions even though the concentration is lower than 0.2%. Check EDTA levels in semen collection tube or other device before use.

All references cited herein are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of detecting the presence of nucleocapsid (N) protein of PRRSV in a sample of biological fluid from a subject, said method comprising
contacting said sample with at least one binding agent which binds the N protein of PRRSV to form at least one complex of binding agent bound to the N protein, and detecting said complex,
wherein the presence of said binding agent in said complex indicates the presence of N protein in said sample.

2. The method of claim 1 wherein said sample of biological fluid is from a subject suspected of being infected with PRRSV.

3. The method of claim 2 wherein said sample is from a porcine subject.

4. The method of claim 1 wherein said biological fluid is selected from blood, serum, plasma, semen, seminal fluid, urine, saliva, tears, mucous, nasal secretions, vaginal secretions, and other bodily fluids or secretions.

5. The method of claim 1 wherein said at least one binding agent comprises an antibody.

6. The method of claim 5 wherein said antibody is a monoclonal antibody.

7. The method of claim 1 wherein said binding agent is labeled.

8. The method of claim 7 wherein said agent is labeled for direct detection.

9. The method of claim 1 wherein said detecting further comprises immobilization of said complex.

10. The method of claim 1 wherein the presence of said binding agent in said complex further indicates the subject as infected with PRRSV.

11. The method of claim 8 wherein said agent is labeled with a particulate label.

12. A method of detecting the presence of nucleocapsid (N) protein of PRRSV in a diluted sample of biological fluid from a subject, said method comprising
   detecting a complex, comprising N protein of PRRSV and at least one binding agent which binds the N protein of PRRSV, said complex formed by contact between said diluted sample with said binding agent,
   wherein the presence of said binding agent in said complex indicates the presence of N protein in said sample.

13. The method of claim 12 wherein said diluted sample is formed by dilution with a diluent containing a divalent cation chelator, EDTA, or from 1-5% bovine serum albumin in 0.01M $KH_2PO_4$ and $Na_2HPO_4$ and sodium azide.

14. The method of claim 12 wherein said sample is from a porcine subject.

15. The method of claim 12 wherein said biological fluid is selected from blood, serum, plasma, semen, seminal fluid, urine, saliva, tears, mucous, nasal secretions, vaginal secretions, and other bodily fluids or secretions.

16. The method of claim 12 wherein said at least one binding agent comprises an antibody.

17. The method of claim 16 wherein said antibody is a monoclonal antibody.

18. The method of claim 12 wherein said binding agent is labeled.

19. The method of claim 18 wherein said agent is labeled with a particulate label.

20. The method of claim 12 wherein the presence of said binding agent in said complex further indicates the subject as infected with PRRSV.

* * * * *

SEQUENCE LISTING

```
<160> NUMBER OF SEQ ID NOS: 6

<210> SEQ ID NO 1
<211> LENGTH: 6
<212> TYPE: PRT
<213> ORGANISM: Porcine reproductive and respiratory syndrome virus

<400> SEQUENCE: 1
```

```
Gln Leu Cys Gln Leu Leu
1               5

<210> SEQ ID NO 2
<211> LENGTH: 17
<212> TYPE: PRT
<213> ORGANISM: Porcine reproductive and respiratory syndrome virus

<400> SEQUENCE: 2

Pro Glu Lys Pro His Phe Pro Leu Ala Ala Glu Asp Asp Ile Arg His
1               5                   10                  15

His

<210> SEQ ID NO 3
<211> LENGTH: 11
<212> TYPE: PRT
<213> ORGANISM: Porcine reproductive and respiratory syndrome virus

<400> SEQUENCE: 3

Ile Ser Thr Ala Phe Asn Gln Gly Ala Gly Thr
1               5                   10

<210> SEQ ID NO 4
<211> LENGTH: 6
<212> TYPE: PRT
<213> ORGANISM: Porcine reproductive and respiratory syndrome virus

<400> SEQUENCE: 4

Gln Leu Cys Gln Met Leu
1               5

<210> SEQ ID NO 5
<211> LENGTH: 17
<212> TYPE: PRT
<213> ORGANISM: Porcine reproductive and respiratory syndrome virus

<400> SEQUENCE: 5

Pro Glu Lys Pro His Phe Pro Leu Ala Thr Glu Asp Asp Val Arg His
1               5                   10                  15

His

<210> SEQ ID NO 6
<211> LENGTH: 11
<212> TYPE: PRT
<213> ORGANISM: Porcine reproductive and respiratory syndrome virus

<400> SEQUENCE: 6

Thr Gln Thr Ala Phe Asn Gln Gly Ala Gly Thr
1               5                   10
```